United States Patent [19]
Oswin et al.

[11] 3,992,267
[45] Nov. 16, 1976

[54] ELECTROCHEMICAL GAS DETECTION METHOD

[75] Inventors: Harry G. Oswin, Chauncey; Keith F. Blurton, Ossining, both of N.Y.

[73] Assignee: Energetics Science, Inc., Elmsford, N.Y.

[22] Filed: Apr. 21, 1975

[21] Appl. No.: 569,851

Related U.S. Application Data

[60] Continuation of Ser. No. 402,733, Oct. 2, 1973, abandoned, which is a division of Ser. No. 88,267, Nov. 10, 1970, Pat. No. 3,776,832.

[52] U.S. Cl. .............................. 204/1 T; 324/30 B
[51] Int. Cl.² .......................................... G01N 27/46
[58] Field of Search ............ 204/1 T, 1 Y, 1 B, 1 N, 204/1 K, 1 F

[56] References Cited
UNITED STATES PATENTS

| | | | |
|---|---|---|---|
| 3,260,656 | 7/1966 | Ross, Jr. | 204/1 |
| 3,278,408 | 10/1966 | Leonard et al. | 204/195 |
| 3,689,394 | 9/1972 | Davies et al. | 204/195 P |

OTHER PUBLICATIONS

R. J. Roethlein et al., J. Electrochem. Soc., vol. 116, pp. 37–40, (1969).
P. Hersch, in "Advances in Analytical Chem. & Instrumentation," vol. 3, (1964), Wiley, N. Y., pp. 185, 234–235.
I. M. Kolthoff et al., Editors, "Treatise on Analytical Chem.," Part 1, vol. 10, p. 6337.
L. Meites, "Polarographic Techniques," Interscience, N. Y., 1955, pp. 205–211.

*Primary Examiner*—John H. Mack
*Assistant Examiner*—Aaron Weisstuch
*Attorney, Agent, or Firm*—Larson, Taylor and Hinds

[57] ABSTRACT

An electrochemical cell comprising an anode, a cathode and a reference electrode operating in an aqueous electrolyte is utilized for detection of noxious gases in air. The gas is oxidized at the anode and detection thereof occurs as a result of the current generated by the reaction. A fixed potential difference is maintained between the anode and the reference electrode to avoid generation of undesired current from reactions involving an oxygen-water redox couple within the cell which would invalidate anode-cathode current for gas detection purposes. The fixed potential is chosen from within the range of about 0.9 to 1.5 volts.

8 Claims, 8 Drawing Figures

ELECTROCHEMICAL GAS DETECTION METHOD

This is a continuation of application Ser. No. 402,733, filed Oct. 2, 1973, now abandoned which is a divisional application of Ser. No. 88,267, filed Nov. 10, 1970, now U.S. Pat. No. 3,776,832.

BACKGROUND OF THE INVENTION

1. Field of the Invention

The present invention relates to electrochemical cells, and particularly to the structure and arrangement of a cell especially suitable for detection and measurement of noxious gases in the atmosphere.

2. Discussion of the Prior Art

In recent times, great awareness has developed regarding the dangers of air pollution, particularly in urban or industrialized areas. As the level of noxious elements in the atmosphere increases, a greater need arises for equipment to detect and measure the quantity of such elements so that their presence in the atmospheres can be reduced or eliminated. In order to meet needs arising in connection with pollution control, extensive activity has been devoted to development and production of equipment useful in solving this problem. For the successful development of such equipment, primary consideration must be accorded to the requirements of commercial and operational feasibility. Although systems may exist which may be considered functionally successful, actual utilization in practical applications has quite often beeen thwarted due to the cost or complexity of such equipment. Therefore, in many cases where beneficial reduction of air pollution has been an important desideratum, its achievement has been rendered impractical by the inordinately complex or costly aspects of the means proposed therefor.

Accordingly, there exists an urgent present need for air pollution control equipment which is both effective in operation and which can be practically utilized in widespread commercial applications without incurrence of excessive cost. This requirement exists in connection with equipment for the detection and measurement for polluting materials, as well as for equipment whereby the quantities of such materials may be controlled or reduced.

The general criteria applied to measuring and testing equipment such as the cell of the present invention include requisites for portability, non-prohibitive cost and accuracy in measuring the quantity of the gas detected. In the prior art, it has been found difficult to simultaneously fulfill all of these requirements. Increasing the accuracy of measuring equipment has inherently involved an increase in either the size or the complexity of such equipment thereby disadvantageously affecting either cost or portability or both. Quite often, problems related to the simultaneous provision of these features have been decisive in obstructing the practical development and utilization of particular detection apparatus.

It is, therefore, considered of significant importance and a valuable contribution to the art of pollution control equipment to provide detection apparatus capable of accurately measuring gas quantity which is also of a relatively convenient size enabling portability, and which does not involve prohibitive cost for its manufacture and practical uitlization.

SUMMARY OF THE INVENTION

Briefly, the present invention may be described as an electrochemical cell for the detection of noxious gases, said cell comprising an anode, a cathode, an aqueous electrolyte, means for exposing the anode to a substance to be detected, means defining a reference potential, and means for maintaining a fixed potential upon said anode relative to said reference potential, said fixed relative potential being from within a range wherein an oxygen-water redox couple within the cell is ineffective to generate current at a level which is discernible relative to the level of current produced therein by a reaction involving the substance to be detected.

By a more specific aspect of the invention, the fixed relative potential is chosen from within the range of about 0.9 to 1.5 volts anodic relative to the hydrogen couple as a zero base.

By another specific aspect of the invention, the cell is constructed to comprise an anode chamber defining a labyrinthine path through which the air is passed to appropriately expose to the anode the substance to be detected. Alternatively, the anode chamber may comprise propeller means for effecting such appropriate exposure.

BRIEF DESCRIPTION OF THE DRAWINGS

A better understanding of the present invention may be had by reference to the following detailed description of the preferred embodiments thereof taken in connection with the accompanying drawings wherein.

DETAILED DESCRIPTION OF A PREFERRED EMBODIMENT

Figure 1:
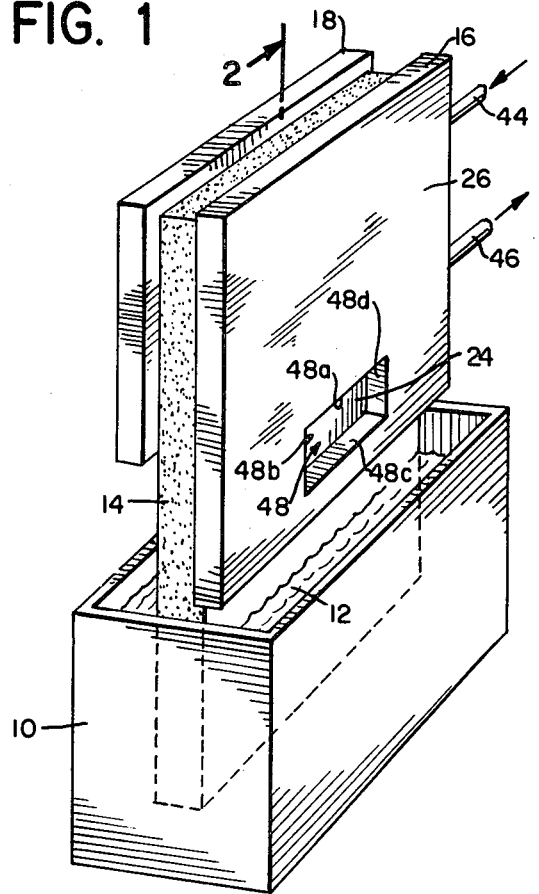
FIG. 1 is a view in perspective of a cell embodying the principles of the present invention.

Referring now in detail to the drawings, there is shown in FIG. 1 an electrochemical detection cell embodying the principles of the present invention which comprises an electrolyte container 10 having a liquid electrolyte 12 therein with an electrolyte matrix 14 extending from within the electrolyte to between the electrodes of the cell. The matrix 14 is formed from fibrous glass material and operates as a wick having the electrolyte absorbed therein in a liquid phase resulting from its continued immersion in the reservoir 12.

A pair of support members 16 and 18 mounted on opposite sides of the electrolyte matrix 14 at the upper end thereof operate to retain, respectively, an anode 20 and a cathode 22 in contact with the electrolyte matrix 14. The anode 20 may be mounted or embedded on the support member 16 in any known manner, with the cathode 22 being similarly mounted upon the support 18. The supports 16 and 18 operate to provide structural mounting for the electrodes 20 and 22 and to maintain the electrodes in operable electrochemical relationship with regard to the electrolyte contained within the matrix 14.

A third or reference electrode 24 is also mounted upon the support member 16, in the same manner as the anode 20 but spaced slightly therebelow, in contact with the electrolyte matrix 14.

The support member 16 is structured to define a labyrinthine path on the interior side thereof upon which the anode 20 is supported. The labyrinthine path is generally designated by the numeral 36 and is defined within a generally rectangular cavity formed by inner walls 28, 30, 32 and 34. A plurality of horizontal spacer members 38, 40 and 42 extend from the sidewalls 30 and 34 in alternating fashion to vertically space the channels of the labyrinthine path 36. An inlet conduit 44 extends through the support member 16 to establish gas flow communication into the labyrinthine path 36 and an outlet conduit 46 permits exit gas to flow out of the labyrinthine path 36.

Figure 2:
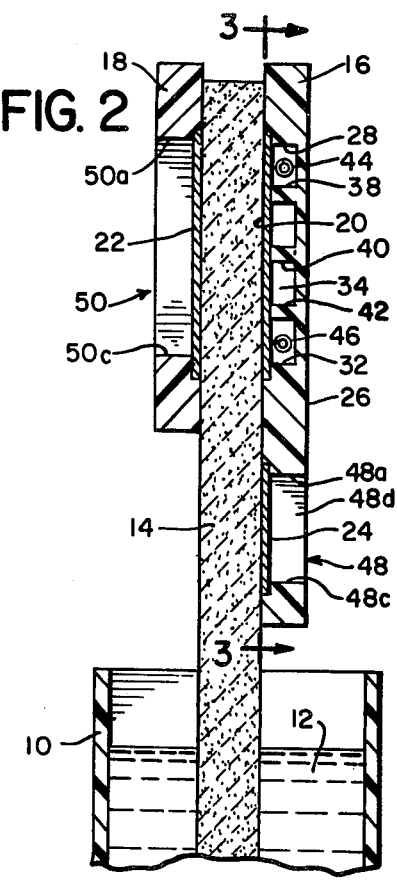
FIG. 2 is a sectional view taken along the line 2—2 of FIG. 1.
Figure 4:
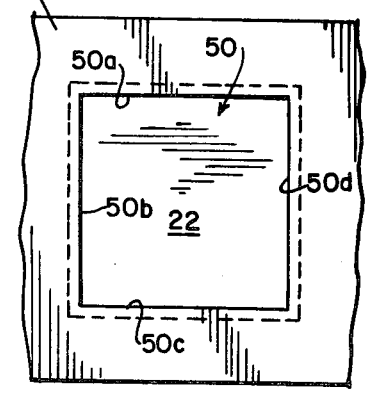
FIG. 4 is a side elevation partially broken away showing the cathode structure of the cell which, in FIG. 1, is out of view on the back side thereof.

At the lower end of the support member 16, there is provided a generally rectangular opening 48 defined by inner walls 48a, 48b, 48c and 48d extending completely through the support member 16 to permit the reference electrode 24 to be exposed to the surrounding atmosphere. Similarly, and as best shown in FIGS. 2 and 4, the support member 18 has defined therethrough a generally rectangular opening 50 bounded by inner walls 50a, 50b, 50c, and 50d, which permits exposure of the cathode 22 to the ambient atmosphere.

In the operation of the electrochemical cell of the present invention, atmospheric air containing a noxious impurity such as carbon monoxide which is to be detected is introduced at a metered rate into the anode chamber defined by the labyrinthine path 36 through the inlet conduit 44. As the air is passed over the anode 20, the electrochemical reaction which occurs by virtue of the exposure of the impurity to the anode 20 will produce a current in the external circuit of the cell thereby enabling detection and measurement of the impurity. Passage through the labyrinthine chamber 36 of air samples containing an impurity to be detected will effect adequate exposure to the anode 20 of the impurity in a manner providing an appropriate reaction rate of the impurity as a result of the fact that the air will be exposed over a relatively constant area of the anode 20.

The requirement that the impurity to be detected be exposed to the anode over a relatively constant anode surface area relates to the obvious necessity for insuring that any change which takes place in the measurement reading of the output circuit occurs as the result of changes in impurity concentration, and not as a result of phenomenon which bears no relationship to the measurements desired. If the change occurs as a result of other factors, not related to or indicative of impurity concentration, the cell will be rendered less accurate or inoperative. Accordingly, it will be understood that exposure of the impurity to the anode in a sporadic or uncontrolled manner which would unpredictably vary the level of anode area exposed, will effect variations in the impurity reaction occurring at the anode thereby adversely effecting the validity of the output reading.

It will also be appreciated that variation in the rate of flow of the air sample through the anode chamber defined by the labyrinthine path 36 can also produce undesired variations in the output reading. Therefore, in the specific embodiment depicted in FIGS. 1–4, the air sample is passed through the labyrinthine path 36 at a metered rate to insure that changes in the output reading are the result of changes in impurity concentration and not caused by unpredictable flow rate variations.

Accordingly, it will be understood that, as a general rule, the cell of the present invention must be operated in a manner to insure that changes in the output reading are a valid and accurate representation of changes in the concentration of the impurity to be measured. Any other factors, such as exposed anode area or air sample flow rate, must either be maintained constant or controlled and counterbalanced in order to negate the net effect thereof, in a manner which will be apparent to those skilled in the art, to insure valid operation of the cell of the present invention.

After having been scrubbed by reaction at the anode 20 of the detected impurity, the air sample is passed out of the anode chamber through the outlet conduit 46.

The basic principles underlying the present invention may be more readily explained by reference in the description of a preferred embodiment to operation of the cell in connection with detection of a particular substance or impurity. Although the principles of the invention may be utilized in cells appropriate for detecting any one of a variety of noxious substances, for the purposes of facilitating the present description it will be assumed that the cell depicted in FIGS. 1–4 is constructed to react and detect carbon monoxide from an air sample passed through the labyrinthine path 36.

Accordingly, in the cell of FIGS. 1–4 arranged for detection of CO, the electrolyte 12 is an aqueous solution of sulfuric acid and is maintained at ambient room temperature. The material chosen for the anode 20 is platinum black, and the electrode shown is a teflon-bonded diffusion electrode, well known to those skilled in the art both as to composition of material and physical structure. Although a variety of other materials may be chosen from within the knowledge of those skilled in the art for the cathode 22 and the reference electrode 24, in the preferred embodiment of FIGS. 1–4, these electrodes are also selected to be teflon-bonded platinum black diffusion electrodes similar to the anode 20.

Figure 5:
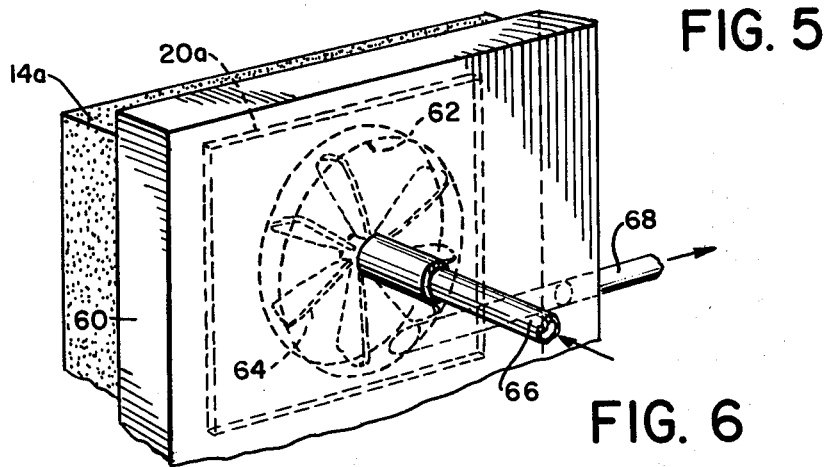
FIG. 5 is a partial view in perspective of an alternative embodiment for the anode chamber of the cell of the invention.

An important requirement of the present invention is the maintenance of a fixed relative potential between the anode 20 and the reference electrode 24. The circuitry whereby this is accomplished is shown in FIG. 5, and a more detailed description of the arrangement and operation thereof will be provided hereinafter. FIG. 5 depicts a potentiostat circuit which is generally arranged in accordance with conventional principles within the knowledge of those skilled in the art and which enables the maintenance of the fixed relative potential between the anode 20 and the reference electrode 24 without development of current flow therebetween. The circuit also operates to enable appropriate current flow in the external circuit between the anode 20 and the cathode 22 when an impurity such as carbon monooxide is reacted within the cell of the invention.

Figure 6:
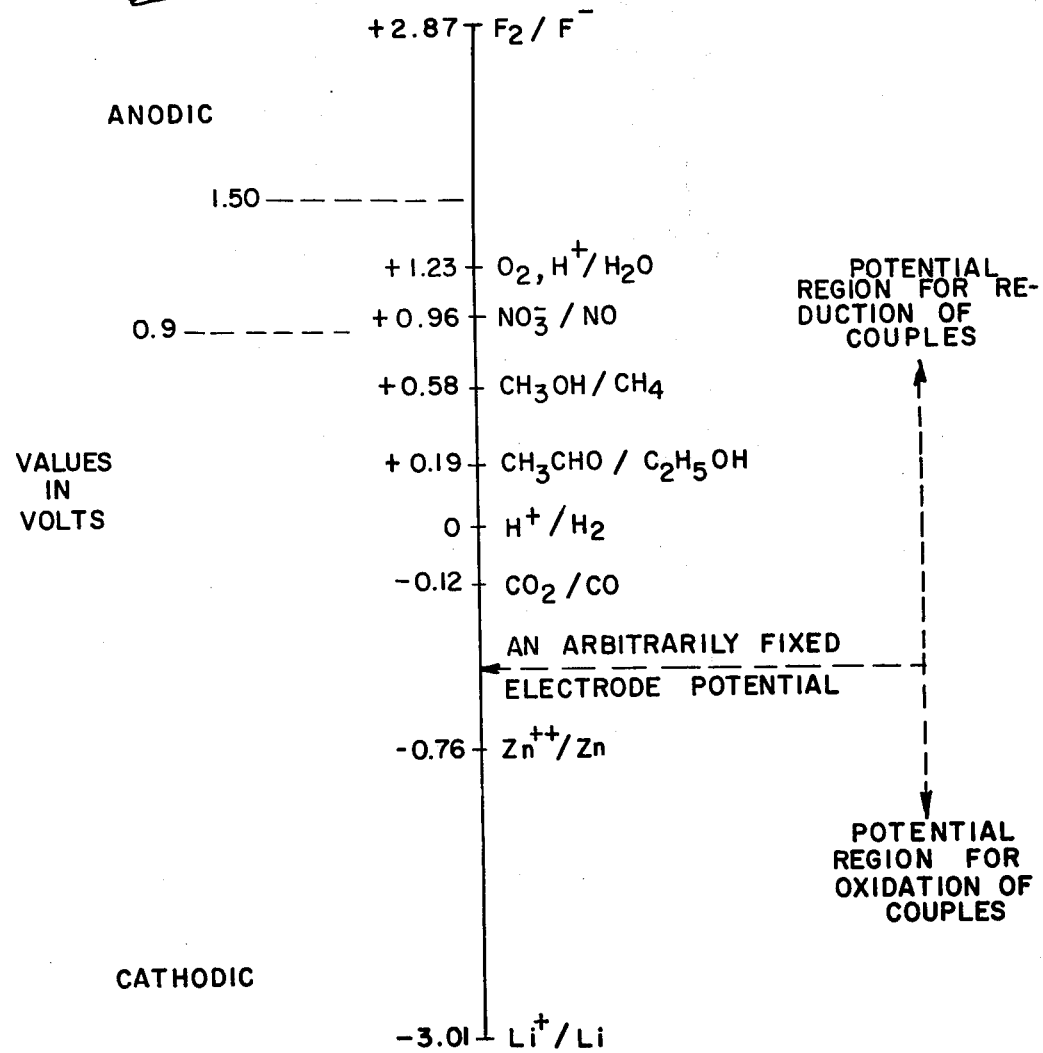
FIG. 6 is a chart derived from the Electromotive Series of Elements indicating for examplary redox couples theoretical relative electrode potentials determining whether a couple will undergo an oxidation or a reduction reaction.

The significance of the fixed relative potential which is maintained between the anode 20 and the reference electrode 24 may be best understood from the chart of FIG. 6 which depicts the relationship between theoretical reversible electrode potential and its affect upon reactions which will take place when certain elements are exposed within a cell to an electrode with an applied potential. The chart of FIG. 6 is derived from the Electromotives Series of Elements, and sets forth by way of example certain electrochemical couples and their theoretical reversible electrode potentials. The electrochemical redox couples are set forth on the right side of a vertical scale with related theoretical electrode potentials indicated therealong on the left side.

The value of the theoretical reversible electrode potential of a redox couple will determine whether the couple will undergo oxidation or reduction as a result of exposure to an electrode having a potential applied thereto. Thus, if a potential is applied to an electrode such that it is more anodic than the reversible electrode potential of the couple, the reduced species of this couple will be oxidized. Conversely, if a potential is applied to an electrode such that it is more cathodic than the reversible electrode potential of the couple, than the oxidized species of this couple will be reduced.

As previously stated, the preferred embodiment of the present invention described herein is arranged to accomplish detection of carbon monoxide in an oxygen containing atmosphere. As shown on the scale of FIG. 6, the $CO_2/CO$ redox couple is indicated as occupying a theoretical level at about $-0.12$ volts relative to the theoretical levels of other couples on the scale. Accordingly, if the cell of FIGS. 1–4 is arranged such that the potential difference which is maintained between the anode 20 and the reference electrode 24 is more anodic than $-0.12$ to a sufficient degree, carbon monoxide exposed at the anode 20 will undergo an oxidation reaction and the $CO_2/CO$ couple will go in the direction indicated by the following formula:

$$CO + H_2O \rightarrow CO_2 + 2H^+ + 2e^-$$

Of course, it will be understood that the degree to which an actually applied potential level must be more anodic or more cathodic than the theoretical reversible electrode potentials will vary depending upon specific circumstances. However, it should be understood that the specific level differences required under practical circumstances will be within the knowledge of those skilled in the art.

One of the problems which may be encountered in the utilization of measuring equipment such as the cell of the present invention relates to the fact that more than one impurity may be exposed to the working electrode of the cell. Accordingly, the reactions which occur at the working electrode would produce current indicative of more than one impurity and it would be impossible to distinguish the presence and quantity of a particular impurity. In most practical applications relating to atmospheric air, the level of carbon monoxide in the air far exceeds the level of other impurities such as nitric oxide and hydrocarbons. Accordingly, in most ordinary situations involving atmospheric air it will be necessary to make provisions to distinguish between the elements in the air since any readings which are generated in the output circuit will be predominantly the result of carbon monoxide presence. Of course, if a very high degree of accuracy is required, or if the level of nitric oxide or hydrocarbons is sufficiently high to invalidate the accuracy of the cell output, provisions must be made to enable the various impurities to be distinctly detected and measured. A manner for accomplishing this would involve passing of an air sample through a series of individual cells, with each of the cells being constructed to react one only of a plurality of impurities with the cell environment being inert to the other impurities. This can be accomplished by appropriate selection of anode and/or cathode materials, the substance for the electrolyte, and the temperature at which the electrolyte is maintained.

Thus, in a situation involving atmospheric air, a series of three cells may be individually structured and appropriately arranged to have an air sample passed therethrough in series in a manner whereby each cell will detect a single impurity. The sequential arrangement of the cells will be important since in some cases a preceding cell will scrub or react all of the impurity contained in an air sample thereby making that impurity unavailable for reaction in a subsequent cell. A more detailed description of an arrangement whereby the individual impurities contained in atmospheric air may be separately detected will be provided hereinafter.

Another more significant problem with regard to generation of undesired unauthentic current in the external circuit, and the problem with which the present invention is primarily concerned, relates to the fact that an oxygen-water redox couple will be potentially available within the cell to produce, in the external circuit, current which is not derived from reaction of the impurity to the detected. Such a redox couple results from oxygen contained in the incoming atmospheric air and water contained in the electrolyte. For example, under certain circumstances water may become oxidized at one of the electrodes of the cell thereby generating current in the external circuit that would not be distinguishable from the current generated by the inpurity reaction. Likewise, oxygen may undergo reduction within the cell thereby similarly generating undesired current.

In accordance with a basic principle of the present invention, an electrochemical cell may be arranged to effectively abate current which might result from reactions of an oxygen-water couple within the cell.

The mechanism of the present invention enabling control within the cell of the oxygen-water couple is the maintenance of a fixed potential upon the anode relative to the reference electrode creating a condition whereby the oxygen-water couple produces in the external circuit no discernable current relative to the current produced by reaction of the impurity. In accordance with the principles of the invention, it has been found that a fixed potential selected from within the range between 0.9 and 1.5 volts relative to the reversible electrode potential of the hydrogen couple will enable achievement of the benefits of the invention.

Referring now to FIG. 6 in order to more clearly understand the specific selection of preferred potential ranges, it will be seen that the oxygen-water redox couple is referenced upon the scale at +1.23 volts. This indicates that at an electrode having a potential more cathodic than +1.23 volts there would occur a reaction involving reduction of oxygen. If the potential of the electrode was chosen to be more anodic than +1.23 volts than oxidation of water would occur at the electrode. Of course, with an electrode potential established in the region between 0.9 and 1.50 volts, any couple in a region more cathodic thereto would undergo oxidation. For example, with a potential in this region, oxidation of CO would invariably occur due to the fact that the $CO_2/CO$ couple is referenced on the scale at $-0.12$ volts, which is a level significantly more cathodic than the level at which the electrode potential would be established.

Figure 7:
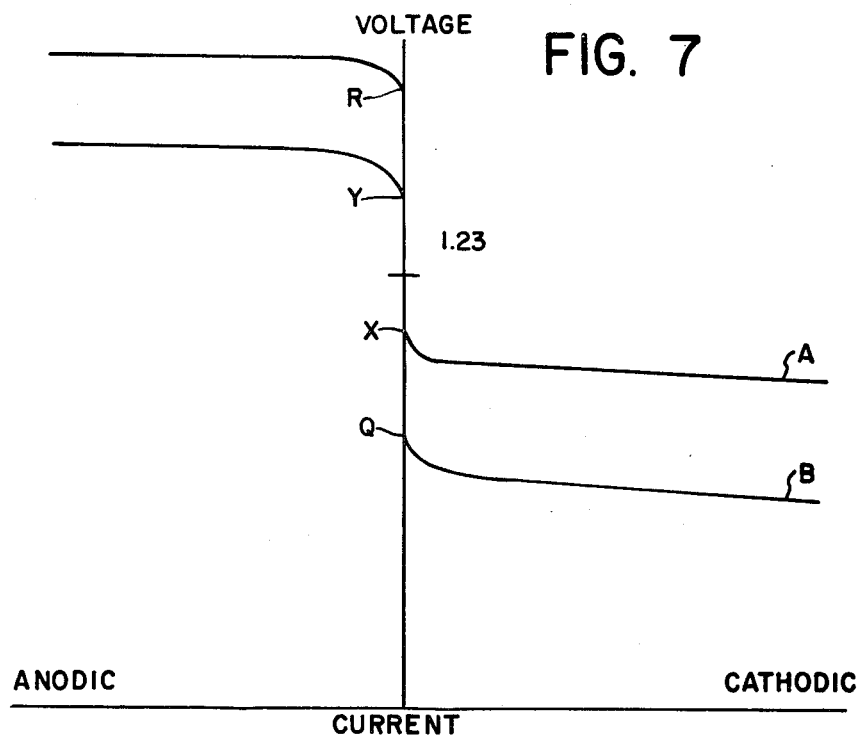
FIG. 7 is a curve depicting the nature of the relationship between current which may be developed in a cell due to an oxygen-water redox couple and applied electrode potential.

The curve of FIG. 7 is intended to depict the general relationship which exists between current developed in a cell due to an oxygen-water redox couple and the level of potential applied to the electrode at which the reactions occur. It will be noted that in curve A, at a level of +1.23 volts no current will be generated as a result of reaction at an electrode charged at that level. As the level of charge upon the electrode is varied, anodic or cathodic current will commence to be generated depending upon the direction in which the potential level is varied. However, it is important to note that in order for there to be generated current of any consequence, it will be necessary that the potential upon the electrode be at a level which varies to a substantial degree from the +1.23 volts level.

The curve labeled A generally depicts the situation which would be developed with an electrode comprising platinum. As seen in FIG. 7, as the potential on such an electrode is varied in a direction either more anodic or more cathodic than +1.23 volts, little or no current will be developed for a range of potential variation between the points labeled $x$ and $y$. Only when the potential upon the electrode of curve A becomes more anodic than the $y$ potential level will there commence to be developed discernable anodic current. Similarly, no discernable cathodic current will be developed until after the potential applied to the electrode of curve A becomes more cathodic than the $x$ potential leve. Thus, it will be understood that if the electrode of curve A has a potential applied thereto which is maintained between the limits $x$ and i $y$, no discernible current will be generated at the electrode as a result of the oxygen-water redox couple.

The shape and nature of the curve of FIG. 7 will depend primarily upon thee choice of electrode material involved. For different electrode materials, curves having basically the same shape as curve A may be developed except that the range of applied potentials across which no discernible oxygen-water redox couple current will be developed may be across wider limits. Additionally, the type of electrolyte involved will likewise effect the specific nature of the curve. For the purposes of the present disclosure, it is not deemed necessary to set forth with great accuracy and detail curves for specific cells since the development of such curves will be within the knowledge of those skilled in the art. However, it is deemed useful to depict the general shape of such curves so that there may be developed a better understanding of the fact that a range of potential level exists within which no discernible oxygen-water redox couple current will be generated.

For the curve labeled A, the levels of $x$ and $y$ may be very approximately assumed to be 1.0 and 1.7 volts for a platinum electrode. The necessity for such a high degree of approximation arises due to the fact that much more than the material of the electrode must be known in order to more accurately establish the value of these levels. Accordingly, the figures set forth are not deemed of significance other than as a general indication of the voltage levels which may bee involved.

A second example of the types of curves which may be generated is the curve labeled B, wherein there is depicted the conditions which would exist with a gold electrode in an acid electrolyte. Again, very approximate levels for the potentials $q$ and $r$ would be, respectively, 0.7 and 1.8 volts. Within this range, no discernible oxygen-water redox couple current would be generated at an electrode having the indicated potential maintained thereupon.

With regard to the selection of electrode material, especially for the working electrode which in the present case is the anode, the material chosen should be such that it will operate effectively within the cell to oxidize the particular impurity to be detected. Obviously, one important requirement of the electrode material will be that it is stable in the cell electrolyte. This and other similar conventional requirements for an electrode material will be apparent to those skilled in the art. Of more pertinence with regard to the application of a fixed relative potential is the characteristic of the electrode material to effect reaction, i.e., oxidation, of the impurity to be detected when the electrode is charged at the fixed relative potential of the present invention. It will be found that different electrode materials will produce differing results to react a given impurity when maintained at a particular electrode potential. This behavior is especially pertinent in connection with the current level generated as a result of the reactivity of the impurity at a particular electrode. In some cases, as a result of the particular choice of electrode material and of the level of potential applied thereto, the reaction of a particular impurity at such an electrode may not proceed at a sufficiently high rate to generate a level of current which will permit an adequate reading in the output circuit to detect and measure the impurity reacted. Accordingly, the selection should be made so that for a given impurity an electrode potential level may be chosen within the limits of the present invention to produce maximum current for a fixed amount of impurity t be reacted. In this manner, the oxygen-water redox couple current may be eliminated by virtue of the fixed electrode potential chosen from within the limits of the invention, i.e., 0.9 to 1.5 volts, with simultaneous enhancement of detection current being provided by virtue of selection of the electrode material which will operate most effectively to react the impurity to be detected at the particular fixed electrode potential utilized.

In the cell of the preferred embodiment of the invention which is depicted in FIG. 1 and which is intended for the purpose of detecting and measuring carbon monoxide, a range of between 1.07 and 1.13 volts is preferred for the anode fixed relative potential. The specific preferred fixed relative potential is 1.1 volts. As previously stated, the preferred material for the anode 20 of this cell is platinum or platinum black and the electrolyte 12 is chosen to be an aqueous solution of sulfuric acid. With these parameters, it will be found that for carbon monoxide there will be generated maximum current when the relative electrode potential is maintained fixed at 1.1 volts. As the fixed relative potential deviates substantially above or below this level the current generated for a fixed quantity of CO reacted will be significantly reduced. Additionally, at 1.1 volts, any slight deviation in the constancy of this fixed relative potential level will produce relatively less variation in current than would be produced if the potential were to be maintained at some other level.

Accordingly, it will be seen that although undesired current from an oxygen-water redox couple may be avoided by maintenance of the fixed relative electrode potential of the present invention, cell accuracy and performance may be enhanced by appropriate selection of other parameters having in mind the criteria set forth herein.

Although platinum and platinum black are set forth as preferred materials for the CO detection cell of FIGS. 1-4, other materials may be suitably utilized. Other materials which would be suitable for utilization in a cell constructed in accordance with the principles of the present invention to detect and measure carbon monoxide may be chosen from the group consisting of platinum, rhodium, iridium, ruthenium, palladium, osmium, tungsten oxide, tungsten carbide, molybdenum oxide, molybdenum sulfide, and alloys or mixtures thereof. In general and as indicated by the aforementioned grouping, it will be found that anode materials for a CO-detection cell may be appropriately selected from the noble metals.

The particular structure and arrangement of a cell formulated within the scope of the present invention may deviate from the specific structure set forth in connection with FIGS. 1-4. The material utilized for the matrix 14 need not necessarily be glass but may be formed to comprise either silica, zirconia, or various polymers. Additionally, the electrolyte need not be immobilized by absorption in a matrix but may be provided in the form of a "free" electrolyte. The important consideration in this connection is, however, that the cell be arranged so that the impurity to be detected and reacted at the working electrode be permitted to migrate to the interface of the electrolyte and the surface of working electrode in order to insure reaction of the impurity thereat. Thus, it would be appropriate, for example, to construct the cell of the present invention having a free electrolyte in contact with one side of the working electrode and exposing the opposite side of the working electrode to the substance, e.g., carbon monoxide, to be detected. The particular structure of the electrodes set forth in the cell of FIGS. 1-4 comprises a teflon-bonded porous electrode, and as a result of the porosity of the electrode the gas to be detected will migrate from the external surface of the electrode, i.e., the surface of anode 20 exposed to the labyrinthine path 36, to the internal surface thereof which is interfaced with the electrolyte, i.e., the opposite surface of anode 20 which is in abutment with the matrix 14. Replacement of the matrix 4 with a free electrolyte arrangement would not impede the reactivity of the cell.

The selection of materials for the cathode and for the reference electrode of a cell constructed within the scope of the present invention may be made within the knowledge of those skilled in the art. Criteria for selection of these materials will relate to commonly known principles of electrochemistry and should be conveniently achievable. For example, the cathode material should, of course, be electronically conducting and have low solubility in the electrolyte. Since, as is true in any electrochemical cell of the type described herein, the reaction occurring at one electrode must be Faradaically equivalent to the opposite redox reaction occurring at the other electrode, it will be understood that to complete the electrolytic cell described herein, a reduction process must occur at the cathode which will be Faradaically equivalent to the oxidation process occurring at the anode. Thus, in an example of the specific cell described in connection with FIGS. 1-4, the material for the cathode should be chosen such that this electrode will be capable of catalyzing water reduction or oxygen reduction or reduction of the appropriate redox couple having its oxidation counterpart occurring at the anode, as for example by the oxidation of CO at the anode 20.

Since the reference electrode is a nonpolarized electrode and does not actively participate in the electrolytic process of the cell, criteria for selection of materials for this electrode woould relate primarily to its ability to cooperate in maintaining the fixed potential relative to the anode and to its general adaptability to the cell environment including, for example, low solubility in the electrolyte.

As shown in the drawings of FIGS. 1-4, both the reference electrode 24 and the cathode 22 are supported in abutment with the electrolyte matrix 14 in a manner whereby their opposite sides are exposed to the ambient atmosphere. With regard to the reference electrode 24, an alternative possibility to this arrangement would be to expose the electrode 24 only to air which has been previously passed through the anode chamber and from which all or a substantial portion of the carbon monoxide has been removed by reaction within the cell. An advantage in using this approach is that it would avoid polarization of the reference electrode 24 which occurs as a result of oxidation of carbon monoxide in the ambient air to which the reference electrode 24 is exposed. Although such polarization occurs in the cell of FIGS. 1-4, it is relatively small due to the fact that there is no appreciable gas flow across the surface of the reference electrode 14 and, accordingly, the effects of oxidation of CO at this electrode while relatively minor and tolerable. The net effect of such polarization is to cause the anode to become more cathodic resulting in lower readings of CO presence in the air sample passed through the anode chamber. Accordingly, the choice of whether to avoid such polarization will depend upon the degree of precision required from the cell and the practicality of incurring the expenditure involved in the achievement of such precision.

Another important aspect of the cell of the present invention relates to the arrangement of the anode chamber through which the substance to be detected is passed for exposure to the anode surface. As previously stated, it is important that conditions of the cell irrelevant to changes in impurity concentration be maintained such that the output reading of the cell is not invalidated thereby.

Figure 3:
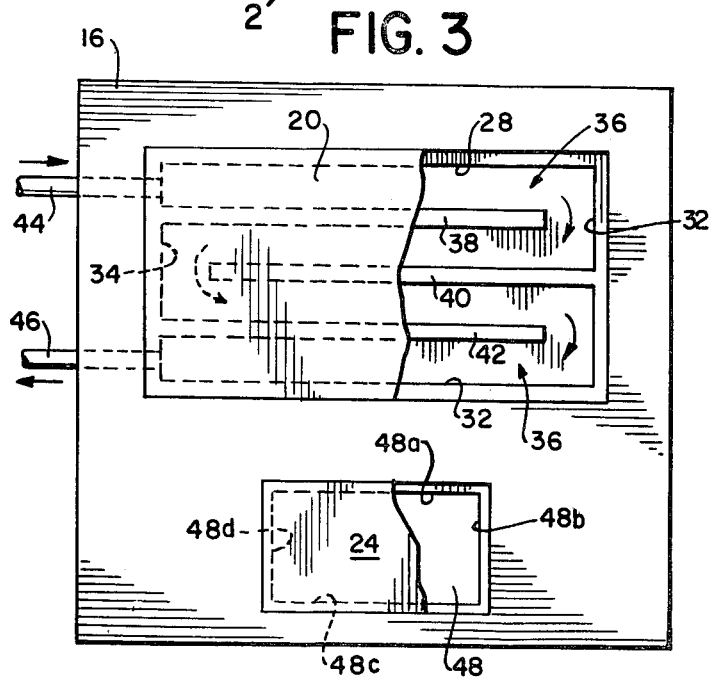
FIG. 3 is a side elevation partially broken away of an interior portion of the cell of FIG. 1 depicting in better detail the anode chamber of the cell.

As previously stated, the anode chamber arrangement is significant in effecting appropriate exposure to the surface of the anode of the oxidizable substance to be detected. In FIGS. 2 and 3, the labyrinthine channel 36 directs the flow path of the CO-bearing air in contact with the anode 20. The shape and configuration of the channel 36 insures that a substantially constant anode area is exposed to the CO, and assuming an appropriate flow rate, the operation of the cell will be such that no changes in the output circuit will occur as a result of sporadic variations in the anode area contacted. Although the labyrinthine channel 36 is considered an appropriate and preferred approach for effecting appropriate exposure of the CO within the anode chamber, alternative arrangements are possible within the scope of the present invention.

One such alternative arrangement is depicted in FIG. 5 which shows a portion of an electrolytic cell constructed in accordance with the present invention and particularly depicting the anode chamber thereof. The cell depicted by FIG. 5 comprises an anode 20a abutting an electrolyte matrix 14a in an identical manner as depicted in FIGS. 1–4. A support member 60 has the anode 20a mounted therein in a manner similar to the mounting of anode 20 upon support member 16. The support member 60, instead of providing the labyrinthine channel 36, defines as an alternative thereto an anode chamber 62 which is generally circular in its configuration and which is fully exposed to the surface of the anode 20a. A propeller mechanism 64 driven to rotate by an appropriate means (not shown) which will be within the knowledge of those skilled in the art, operates to swirl air within the anode chamber 62 thereby to enhance the scrubbing effect prduced upon the surface of the anode 20a. The inlet means whereby air is introduced into the anode chamber 62 comprise a centrally located conduit 66 defined internally of the shaft of propeller 64 in flow communication with the anode chamber 62. An exit conduit 68 extending in flow communication from the sidewall of chamber 62 permits the contents of chamber 62 to pass therefrom in a direction tangentially of said sidewall. Thus, air entering the anode chamber 62 through the central conduit 66 will be swirled about the chamber by the action of the propeller 64 thereby effecting oxidation of CO as a result of contact with the anode surface. Subsequently, the air will be emitted through the conduit 68 by virtue of the swirling motion emparted thereto by the propeller 64.

The operation of a cell structured in accordance with FIG. 5 is again effective to achieve an appropriate distribution across the surface of the anode 20a of CO contained in the air introduced into the anode chamber 62. A valid current reading may be obtained in the output circuit of the cell of FIG. 5 due to the fact that the CO is uniformly distributed over a fixed anode surface area. Such fixed uniform distribution operates in essentially the same manner as the labyrinthine channel 36 of FIGS. 1–4 to insure that changes in exposed anode surface area do not operate to produce erroneous indications of CO concentration in the output circuit readings. The specific embodiment of FIG. 5 is considered especially appropriate for utilization with applications involving relatively lower CO concentrations since it operates to increase current levels for a given CO concentration thereby enhancing the effectiveness of the external circuit readings as indications of the presence and quantity of CO.

Figure 8:
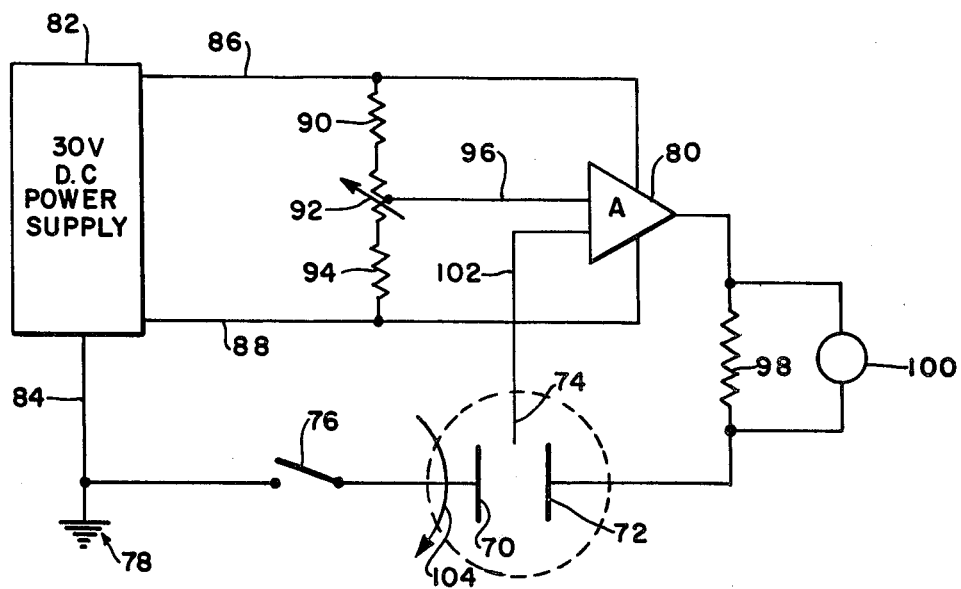
FIG. 8 is a schematic diagram of a potentiostat circuit for controlling operation of the cell and particularly as applied in maintaining a fixed relative potential difference between the cell anode and a reference electrode.

The maintenance of constant potential between the anode and the reference electrode of the cell of the invention is accomplished by a potentiostat circuit, connected to the cell in the manner depicted in FIG. 8, which is conventional and within the knowledge of those skilled in the art. The potentiostat circuit of FIG. 8 operates to maintain a constant relative potential between the anode and the reference electrode.

In FIG. 8, the electrochemical cell of the invention is shown schematically as comprising an anode 70, a cathode 72, and a reference electrode 74, with the anode connected through a switch 76 to ground potential 78. The circuit basically comprises an operational amplifier 80 having both the reference electrode 74 and the cathode 72 connected thereto. A DC power supply 82 having a connection 84 to ground potential 78 is connected to the amplifier 80 through leads 86 and 88 with resistors 90, 92, and 94 connected thereacross in parallel between the power supply 82 and the amplifier 80. Resistor 92 comprises a rheostat and is connected to the amplifier 80 through a lead 96 whereby adjustment of the resistor 92 enables adjustment of the fixed relative potential which is to be maintained between the reference electrode 74 and the anode 70. The cathode 72 is connected to the amplifier 80 through a resistor 98 having a voltmeter 100 connected theracross. The reference electrode 74 is connected to the operational amplifier 80 through a lead 102 and as the relative potential between the reference electrode 74 and the anode 70 develops a tendency to vary from the fixed level established by adjustment of rheostat 94, the amplifier 80 operates through a negative feedback to maintain constant the relative potential between the anode 70 and the reference electrode 74. The factor creating the tendency to alter the anode-reference electrode fixed relative potential is developed as a result of reaction at the anode 70 of the impurity to be detected, i.e., oxidation of CO contained within the air sample flowing across the face of the anode 70 as indicated by the arrow 104. The output current of the operational amplifier 80 will pass through the resistor 98 and will be a result of and related to the level of oxidation of CO occurring at the anode 70. Therefore, the reading taken at the voltmeter 100 will be representative of the oxidation reaction occurring at the anode 70 and of the quantity of material oxidized. The voltmeter 100 may be readily calibrated in a known manner to provide determination of the quantity of CO occurring in the air sample taken, and if the conditions in the anode chamber are in accordance with the teachings previously set forth, appropriate readings may be generated pursuant to the principles of operation provided.

Both the potentiostat circuit of FIG. 8, and the operational amplifier 80 included therein, are considered fully conventional and within the knowledge of a skilled artisan.

It should be understood that any diviation which might occur in the relative potential difference between the anode and the reference electrode will affect the accuracy and precision of the cell. Accordingly, the extent of deviation which may be tolerated will depend upon the degree of precision required for a particular application. The potentiostaat circuit of FIG. 8 is considered to provide a degree of constancy for the relative electrode potential difference which will be adequate for most applications in connection with atmospheric air. Where a higher degree of precision may be required circuitry other than that of FIG. 8, which may be more precisely constructed to insure greater accuracy, may be used.

Furthermore, it should be appreciated that although the invention is importantly characterized by the maintenance of a constant or fixed relative potential difference, deviations in said fixed relative potential may occur within the concepts of the present invention and without departure from the scope and purview thereof.

As previously stated, impurities other than carbon monoxide may be measured and detected by cells constructed in accordance with the present invention. For example, by providing certain modifications which may relate to either the material of the electrode, the electrolyte composition, or the temperature of the electrolyte, and appropriately adjusting the fixed relative potential between the anode and the reference electrode, a cell may be adapted to oxidize a specific impurity in a manner whereby other impurities simultaneously contained in an air sample will be inert to the cell environment. Inasmuch as nitric oxide and hydrocarbons are the two most significant elements, in addition to carbon monoxide, which may be usually present in atmospheric air, it is considered appropriate to describe, as examples of cell modifications, arrangements whereby these elements may be measured, detected and removed from an air sample.

Accordingly, assuming a system wherein it was desired to measure and detect all three of the more significant impurities present in atmospheric air, i.e., carbon monoxide, nitric oxide and hydrocarbons, this could be accomplished by a three-cell arrangement comprising a separate cell to individually detect and react each of these impurities. Normally, it would be most appropriate to pass the air sample first through a cell for detection of the nitric oxide. Such a cell should preferably comprise a gold anode and a sulfuric acid electrolyte maintained at room temperature. In this cell, the fixed relative potential to be maintained between the anode and the reference electrode should preferably be from within the range between 1.0 and 1.3 volts. As a result of passage through the anode chamber of such a cell, the air sample would have removed therefrom all or most of the nitric oxide contained therein by oxidation at the anode of the cell. The current developed in the external circuit of the cell as a result of such oxidation would ooperate in the same manner as previously described in connection with FIGS. 1–4 for detection of carbon monoxide, and, accordingly, detection and measuring of the nitric oxide, as well as removal of all or of a substantial portion thereof from the air sample, could be accomplished.

Subsequent to passage through the nitric oxide detection cell, the air sample would be passed to the cell for detection and oxidation of carbon monoxide. Such a cell, comprising a platinum electrode and an electrolyte consisting of sulfuric acid at amibient temperature, may be returned in accordance with the description previously set forth in connection with FIG. 1–4.

A third cell for the detection and measurement of hydrocarbons in the air sample should preferably comprise a platinum black electrode and an electrolyte consisting of phosphoric acid at a temperature within the range between 100° C and 200° C. The fixed potential maintained between the anode and the reference electrode should be preferably from within the range between 1.05 and 1.15 volts. The air emitted from the CO-detection cell should be introduced into the third cell for detection of hydrocarbons, with oxidation of the hydrocarbons occurring at the anode in a manner similar to that previously described, to produce external current indicating hydrocarbon presence and the amount thereof.

Of course, each of the three cells described should include a potentiostat circuit to maintain the fixed relative potential between the anode and the reference electrode, in the manner previously described. In each case, undesired current produced by an oxygen-water couple would be problematic and could be dealt with and avoided in accordance with the principles of the present invention from the description previously set forth herein.

As has been stated, because of the specific structure and arrangement of each individual cell, no problems will arise in any one of the cells from undesired detection current caused by presence and reaction of an impurity which is not to be detected by that particular cell. For instance, in the foregoing arrangement utilizing three cells, the air samples are first passed through the nitric oxide detection cell. The presence in this cell of CO and hydrocarbons will not adversely affect the validity of the current in the external circuit as a measurement of NO presence due to the fact that neither carbon monoxide nor hydrocarbons will be oxidized in this cell since these elements are inert to the gold anode of the cell. Similarly, the air passed through the carbon monoxide cell will not involve oxidation of either nitric oxide or hydrocarbons. Nitric oxide woould normally be reactive in the CO cell, but since this element has either been removed or reduced to insignificant amounts as a result of passage through the first No detection cell, no problem arises. The hydrocarbons require an electrolyte other than sulfuric acid at ambient temperature for oxidation to occur and, accordingly, their presence in the CO cell will not effect a reaction. Therefore, it will be seen that the problem of plural impurities in an air sample which could obstruct the accurate detection of a single impurity is readily dealt with in the manner described by appropriate selection of cell conditions, i.e., fixed relative potential and anode and electrolyte characteristics, and by appropriate sequential arrangement of the cells. The problem of undesired current generated as a result of the oxygen-water couple which has also been problematic, will also be readily avoided by the application of the appropriate fixed relative potential in accordance with the principles of the present invention in the manner herein described.

Fron the foregoing it should be apparent that the principles of the present invention will have broad application in cells utilized in a variety of environments for various purposes. Although the foregoing description has been limited to the detection and measuring of impurities in atmospheric air, it should be understood that the invention need not be so limited although this will probably be its most important area of application.

Other areas of application for the present invention could be in connection with industrial equipment, for example, process plants which require detection and measurement of certain gaseous substances. In connection with this type of application, it is important to note that the substance to be detected may be exposed to the surface of the working electrode of the cell without oxygen presence. This would not adversely affect the operation of the cell in detecting a particular impurity or gaseous substance. Since the cell would comprise an aqueous electrolyte, the impurity exposed at the interface of the electrolyte and the working electrode would be oxidized thereby generating detection current. It will be clear that exposure to the anode of the impurity alone or of the impurity without oxygen, will not impede occurrence of a detection reaction. Furthermore, removal or absence of oxygen from the impurity-bearing environment would operate to obviate the necessity for the lower limit of 0.9 volts in the establishment of the fixed relative potential between the working electrode and the reference electrode. It will be understood that this lower limit is established to insure avoidance of oxygen reduction in the coil which would generate undesired current. Since in the exemplary industrial application referred to no oxygen may be available to effect this reaction, the problem will not arise and the requirement for the lower limit is removed. However, the requirement for the upper limit of 1.5 volts would remain due to the fact that oxidation of the water in the electrolyte would be a possibility to be avoided. Accordingly, it will be clear that where the impurity to be detected is not exposed to the working electrode in an oxygen-containing environment, the limits of the present invention may be defined by a fixed relative potential between the working electrode and the reference electrode which is not more anodic than +1.50 volts.

Another specific embodiment of the present invention may have application in the detection and measurement of the level of alcohol in a person's breath. Such a cell would be primarily arranged to measure and detect ethanol although methanol would also be detectable with such a cell. In the specific embodiment of a cell for the detection of ethanol/methanol, sulfuric acid in an aqueous solution would be the preferred electrolyte and the range of fixed relative potential between the anode and the reference electrode would be preferably between 1.05 and 1.3 volts.

Although in the foregoing description the present invention has been described by reference to specific preferred embodiments thereof, it is to be understood that modifications and alterations in the structure and arrangement of the invention, other than those set forth herein, may be achieved within the knowledge skilled in the art and that such modifications and alterations are to be considered as within the scope and purview of the invention.

What is claimed is:

1. The method of quantitatively detecting a gaseous noxious atmospheric pollutant selected from the group consisting of carbon monoxide, nitric oxide, hydrocarbons, ethanol and methanol in air in an electrochemical cell comprising an anode, a cathode, a reference electrode through which no substantial current flows, said anode being selected from the group consisting of platinum, rhodium, iridium, ruthenium, palladium, osmium, tungsten oxide, tungsten carbide, molybdenum oxide, molybdenum sulfide, and alloys or mixtures thereof, and an aqueous electrolyte in contact with said anode, cathode, and reference electrode including the steps of (1) feeding an air sample containing the noxious gas to be detected to the anode of said cell, said sample being substantially free of other noxious gases; (2) maintaining said anode at a fixed potential of from about 0.9 to 1.5 volts with respect to the reversible hydrogen couple in the electrolyte of said cell relative to said reference electrode to oxidize said noxious gaseous substance and simultaneously insure that current due to oxygen reduction or water oxidation within said electrochemical cell is not discernible relative to the level of current produced by said oxidation of gaseous substance; and (3) measuring the current flowing between said anode and cathode of said cell to quantitatively determine the amount of said gaseous substance to be detected in said gaseous sample.

2. The method of claim 1 wherein the fixed potential of said anode is maintained at a potential of from about 1.07 to 1.13 volts.

3. The method according to claim 1 wherein the anode of the electrochemical cell is a Teflon-bonded diffusion electrode.

4. The method of claim 1 wherein the electrolyte is phosphoric acid.

5. The method of claim 1 wherein the electrolyte is alkali hydroxide.

6. The method of claim 1 wherein the electrolyte of said electrochemical cell is maintained in a matrix.

7. The method of claim 1 wherein the electrolyte of said electrochemical cell is free flowing.

8. The method of claim 1 wherein the noxious gas is carbon monoxide.

* * * * *